(12) United States Patent
Kumar et al.

(10) Patent No.: US 7,994,343 B2
(45) Date of Patent: Aug. 9, 2011

(54) PROCESS FOR THE PRODUCTION OF ATORVASTATIN CALCIUM IN AMORPHOUS FORM

(75) Inventors: Yatendra Kumar, Haryana (IN); Saridi Madhava Dileep Kumar, Haryana (IN); Swargam Sathyanarayana, Andhra Pradesh (IN)

(73) Assignee: Ranbaxy Laboratories Limited, New Delhi (IN)

( * ) Notice: Subject to any disclaimer, the term of this patent is extended or adjusted under 35 U.S.C. 154(b) by 667 days.

(21) Appl. No.: 10/549,890

(22) PCT Filed: Nov. 19, 2004

(86) PCT No.: PCT/IB2004/003789

§ 371 (c)(1),
(2), (4) Date: Oct. 6, 2008

(87) PCT Pub. No.: WO2005/092852

PCT Pub. Date: Oct. 6, 2005

(65) Prior Publication Data

US 2010/0197941 A1    Aug. 5, 2010

(51) Int. Cl.
*C07D 207/416*    (2006.01)

(52) U.S. Cl. .................................................. 548/537

(58) Field of Classification Search ............ 548/537
See application file for complete search history.

(56) References Cited

U.S. PATENT DOCUMENTS

| | | | |
|---|---|---|---|
| 5,003,080 A | 3/1991 | Butler et al. | 548/517 |
| 5,097,045 A | 3/1992 | Butler et al. | 549/373 |
| 5,103,024 A | 4/1992 | Millar et al. | 549/373 |
| 5,124,482 A | 6/1992 | Butler et al. | 564/169 |
| 5,149,837 A | 9/1992 | Butler et al. | 549/333 |
| 5,155,251 A | 10/1992 | Butler et al. | 558/442 |
| 5,216,174 A | 6/1993 | Butler et al. | 548/517 |
| 5,245,047 A | 9/1993 | Butler et al. | 548/517 |
| 5,248,793 A | 9/1993 | Millar et al. | 549/375 |
| 5,273,995 A | 12/1993 | Roth | 514/422 |
| 5,280,126 A | 1/1994 | Butler et al. | 548/517 |
| 5,342,952 A | 8/1994 | Butler et al. | 546/245 |
| 5,397,792 A | 3/1995 | Butler et al. | 514/326 |
| 5,686,104 A | 11/1997 | Mills et al. | |
| 6,528,660 B1 | 3/2003 | Kumar et al. | 548/537 |
| 6,613,916 B2 | 9/2003 | Pflaum | 548/537 |
| 6,646,133 B1 | 11/2003 | Greff et al. | 548/537 |
| 2002/0183378 A1 | 12/2002 | Aronhime et al. | 514/423 |
| 2003/0109569 A1 | 6/2003 | Sorsak | 514/423 |
| 2004/0077708 A1 | 4/2004 | Grahek et al. | 514/423 |

FOREIGN PATENT DOCUMENTS

| | | |
|---|---|---|
| CA | 2392025 | 6/2001 |
| CA | 2456095 | 3/2003 |
| EP | 1 148 049 | 10/2001 |
| WO | WO 97/03960 | 2/1997 |
| WO | WO 00/71116 | 11/2000 |
| WO | WO 01/28999 | 4/2001 |
| WO | WO 01/42209 | 6/2001 |
| WO | WO 01/93860 | 12/2001 |
| WO | WO 02/41834 | 5/2002 |
| WO | WO 02/051804 | 7/2002 |
| WO | WO 02/057225 | 7/2002 |
| WO | WO 02/057228 | 7/2002 |
| WO | WO 02/083637 | 10/2002 |
| WO | WO 02/083638 | 10/2002 |
| WO | WO 03/004470 | 1/2003 |
| WO | WO 03/011826 | 2/2003 |
| WO | WO 03/018547 | 3/2003 |
| WO | WO 03/068739 | 8/2003 |
| WO | WO 03/078379 | 9/2003 |
| WO | WO 03/099785 | 12/2003 |
| WO | WO 2004/085391 | 10/2004 |
| WO | WO 2006/037125 | 4/2006 |

OTHER PUBLICATIONS

Pavia et al. Introduction to Organic Laboratory Techniques 1990, pp. 577-596.*
Brower et al, "The Synthesis of (4R-cis)-1,1-Dimethylethyl 6-cyanomethyl-2,2-dimethyl-1,3-dioxane-4-acetate, a Key Intermediate for the Preparation of CI-981, a Highly Potent, Tissue Selective Inhibitor of HMG-CoA Reductase", *Tetrahedron Letters*, 33(17):2279-2282 (1992).
Shimako et al, "Atorvastatin (CI-981) Clinical Pharmacokinetic Study (I): Relative Bioavailability of Amorphous and Crystalline Preparations of Atorvastatin", *Japanese Pharmacology and Therapeutics*, 26(8):1241-1252 (1998).
Wade et al., "In Pursuit of Higher Purity: Use of $^{13}$C NMR and $^{13}$C-Enriched Substrates to Trace Impurity Generation and Removal in the Synthesis of Atorvastatin", *Organic Process Research and Development*, 1(4):320-324 (1997).

* cited by examiner

*Primary Examiner* — Jason M Nolan

(57) ABSTRACT

A process for the production of amorphous atorvastatin calcium and stabilized, amorphous atorvastatin calcium is provided.

47 Claims, No Drawings

PROCESS FOR THE PRODUCTION OF ATORVASTATIN CALCIUM IN AMORPHOUS FORM

FIELD OF THE INVENTION

Processes for the production of atorvastatin calcium of high purity in an amorphous form are provided.

BACKGROUND OF THE INVENTION

Atorvastatin is known by the chemical name [R—(R*, R*)]-2-(4-fluorophenyl)-β,δ-dihydroxy-5-(1-methylethyl)-3-phenyl-4-[(phenylamino)carbonyl]-1H-pyrrole-1-heptanoic acid. The hemi-calcium salt of atorvastatin is useful as an inhibitor of the enzyme 3-hydroxy-3-methylglutaryl-coenzyme A reductase (HMG-CoA reductase) and is thus useful as a hypolipidemic and hypocholesterolemic agent.

U.S. Pat. Nos. 5,273,995; 5,003,080; 5,097,045; 5,103,024; 5,124,482; 5,149,837; 5,155,251; 5,216,174; 5,245,047; 5,248,793; 5,280,126; 5,397,792; and 5,342,952, disclose various processes and intermediates for preparing atorvastatin. Several processes have been reported for the preparation of amorphous form of atorvastatin calcium in U.S. Pat. Nos. 6,528,660 and 6,613,916; U.S. Patent Application Publication Nos. 2002/183378 and 2003/109569; and International (PCT) Patent Applications WO 01/2899, WO 02/57228, WO 02/83637, WO 02/83638, WO 03/18547 and WO 03/68739.

SUMMARY OF THE INVENTION

In one embodiment, a process for the production of atorvastatin calcium in amorphous form is provided comprising:
a) reacting a solution of (4R-cis)-1,1-dimethylethyl-6-{2-[2-(4-fluorophenyl)-5-(1-methylethyl)-3-phenyl-4-[(phenylamino)-carbonyl]-1H-pyrrol-1yl]ethyl}-2,2-dimethyl-1,3-dioxane-4-acetate (Compound H, as shown in Scheme I) in a water miscible solvent with an acid to obtain [R—(R*,R*)]-1,1-dimethylethyl-2-(4-fluorophenyl)-β,δ-dihydroxy-5-(1-methylethyl)-3-phenyl-4-[(phenylamino)carbonyl]-1H-pyrrole-1-heptanoate (Compound I, as shown in Scheme I);
b) treating Compound I with an alkali metal hydroxide to obtain an alkali metal salt of atorvastatin;
c) washing the solution of alkali metal salt of atorvastatin with a solvent immiscible or slightly miscible in water;
d) treating the washed solution of alkali metal salt of atorvastatin with a calcium salt or calcium hydroxide to obtain atorvastatin calcium;
e) isolating crude atorvastatin calcium;
f) purifying crude atorvastatin calcium by dissolving in a mixture of tetrahydrofuran and methanol, and precipitating with water to obtain pure atorvastatin calcium in crystalline form; and
g) converting crystalline pure atorvastatin calcium so obtained into amorphous form.

SCHEME I

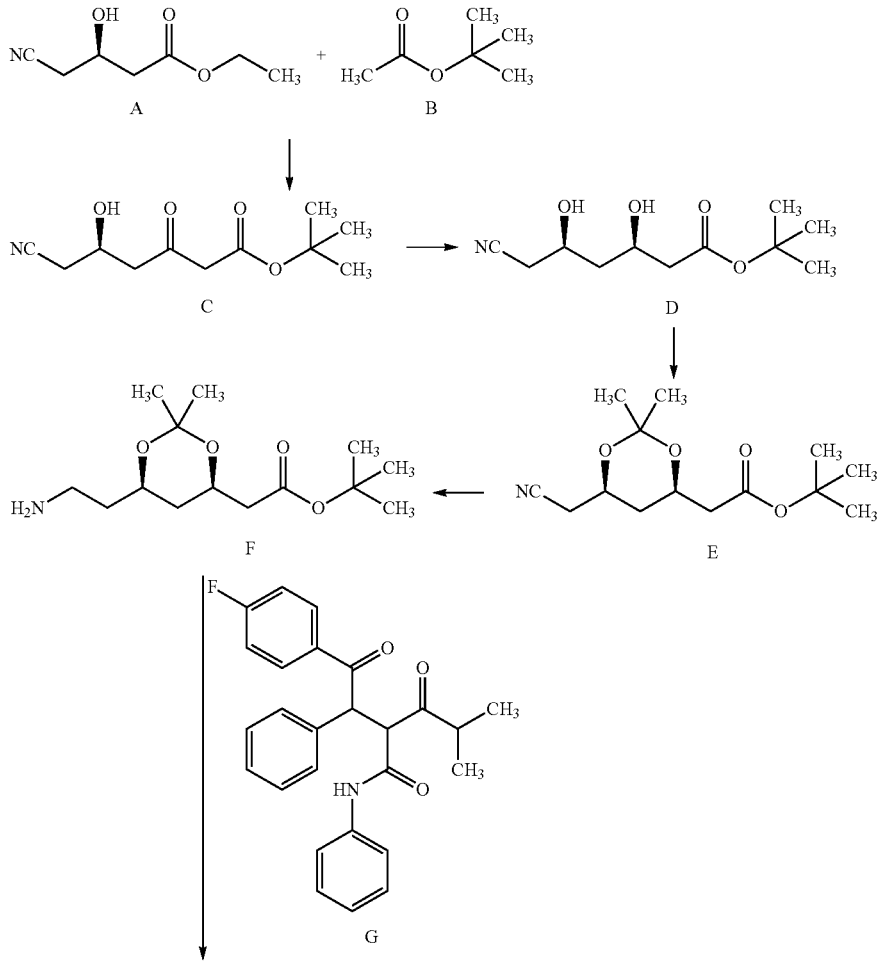

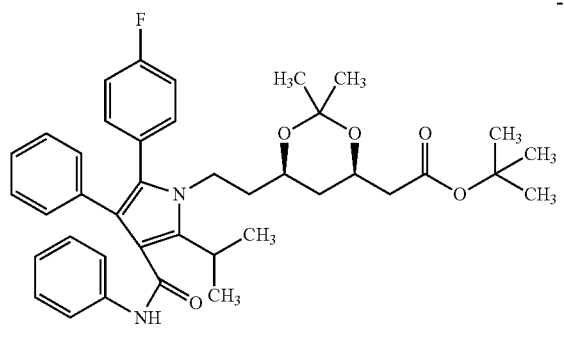

H

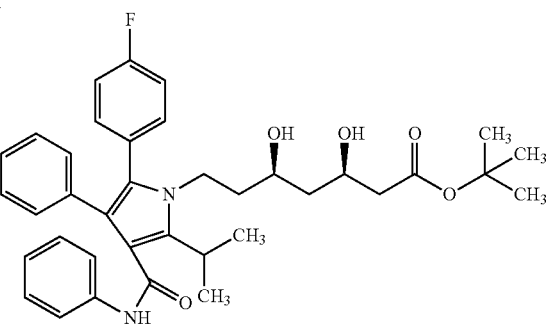

I

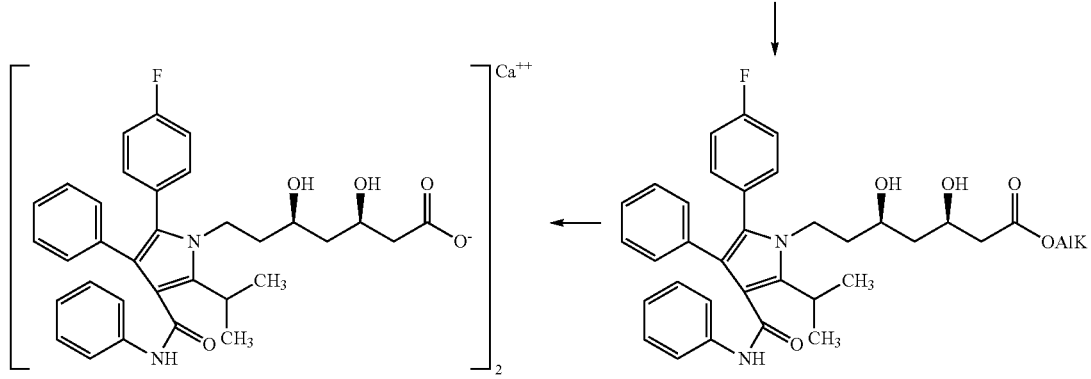

In another embodiment, a process for purifying atorvastatin calcium is provided comprising dissolving crude atorvastatin calcium in a mixture of tetrahydrofuran and methanol, and precipitating with water to obtain pure atorvastatin calcium in crystalline form.

In an additional embodiment, a process for the production of stabilized atorvastatin calcium in amorphous form is provided comprising:
a) dissolving crystalline atorvastatin calcium and an antioxidant in a solvent;
b) adding the solution of atorvastatin calcium and antioxidant to an anti-solvent; and
c) separating precipitated, amorphous atorvastatin calcium from the resulting suspension.

In yet another embodiment, a process for the production of atorvastatin calcium in amorphous form is provided comprising:
a) dissolving crystalline atorvastatin calcium in a hydroxylic solvent;
b) adding the obtained solution of atorvastatin calcium to a non-hydroxylic anti-solvent, wherein the non-hydroxylic anti-solvent has a higher boiling point than the hydroxylic solvent;
c) concentrating the solution so obtained to remove the hydroxylic solvent; and
d) separating precipitated amorphous atorvastatin calcium from the resulting suspension.

The acid used for deketalization of Compound H to afford Compound I may be an inorganic acid. Examples of inorganic acids include hydrochloric, hydrobromic, sulphuric, phosphoric and nitric acids. Suitable water-miscible solvents for the deketalization process include acetonitrile; alcohols such as methanol, ethanol, propanol, and isopropanol; cyclic ethers such as dioxane and tetrahydrofuran; ketones such as acetone and mixtures thereof.

Compound I can be hydrolysed with an alkali metal hydroxide such as sodium hydroxide, potassium hydroxide and lithium hydroxide. The reaction mixture may be maintained at a pH of at least 9, for example, about 12, to result in efficient hydrolysis and to minimize side product formation. The reaction mixture is then washed with a water-immiscible or slightly water-miscible solvent to remove unreacted compounds and other impurities. Suitable solvents for the washing include ethers such as methyl tertiary butyl ether, diethyl ether, methyl ethyl ether and dibutyl ether; esters such as ethyl acetate and isopropyl acetate; and hydrocarbons such as toluene and petroleum ether.

The solution of alkali metal salt of atorvastatin obtained is reacted with calcium hydroxide or a calcium salt such as calcium acetate, calcium chloride, calcium sulfate, calcium nitrate and calcium phosphate. The reaction may be performed at a temperature of about 45 to 55° C. The pH of the solution of alkali metal salt of atorvastatin may be lowered to about 7.8 to 8.2 with an acid before addition of the calcium salt to facilitate isolation of crude atorvastatin calcium.

Any residual water-immiscible or slightly water-miscible solvent remaining in the reaction mixture may be removed under reduced pressure to aid precipitation. Water may be used as an antisolvent to effect precipitation of crude atorvastatin calcium in good yields. Water may be added at a temperature of about 55 to 65° C. to avoid rapid precipitation and seeds of crystalline atorvastatin calcium may also be added to the mixture. Crude atorvastatin calcium may be isolated in high yields by cooling the reaction mixture to a temperature of about 20 to 35° C. and stirring at the same temperature for several hours before filtration or centrifugation.

Crude atorvastatin calcium is purified by crystallization using tetrahydrofuran and methanol as solvents and water as anti-solvent. Purification involves removal of unreacted compounds, side product and other impurities. Tetrahydrofuran, methanol and water may be used in the volume ratio 1:1:4 to obtain atorvastatin calcium of high purity. Water may be added at a temperature of about 60 to 65° C. Seeds of crystalline atorvastatin calcium may be added to facilitate precipitation. In a particular embodiment, seeds of crystalline atorvastatin calcium are added at a temperature of about 50° C. Crystalline atorvastatin calcium may be isolated by cooling the mixture to a temperature of about 30 to 35° C. and stirring at the same temperature for several hours before filtration or centrifugation.

Crystalline pure atorvastatin calcium may be converted into the amorphous form by methods known in the art such as U.S. Pat. Nos. 6,528,660 and 6,613,916; International (PCT) Patent Applications WO 01/28999, WO 03/99785, WO 03/78379, WO 03/18547 and WO 02/57228; and U.S. Patent Application Publication No. 2002/183378, which are incorporated herein by reference.

Amorphous atorvastatin calcium may also be obtained by having an additional step wherein the pure crystalline atorvastatin calcium (where "pure" is meant in the sense of chemical purity) obtained after step f) is suspended in a mixture of methanol and water in the volume ratio 1 to 5 and stirred with seed crystals of crystalline Form I, to obtain atorvastatin calcium in crystalline Form I. The stirring may be performed at a temperature of about 10 to 65° C., for example, about 30 to 45° C.

Alternatively, pure crystalline atorvastatin calcium (where "pure" is meant in the sense of chemical purity) obtained after step f) is suspended in a mixture of methanol and water in the volume ratio 3 to 2 and stirred with seed crystals of crystalline Form II, to obtain atorvastatin calcium in crystalline Form II. The volume of methanol and water mixture may be about 15 to 25 times, for example, about 20 times, the weight of the atorvastatin calcium to be suspended. The stirring may be performed at a temperature of about 10 to 65° C., for example, about 25 to 45° C.

In yet another variant, a further additional step may be performed wherein crystalline Form I of atorvastatin calcium obtained above is suspended in a mixture of methanol and water in the volume ratio 3 to 2 and stirred with seed crystals of crystalline Form II, to obtain atorvastatin calcium in crystalline Form II. The volume of methanol and water mixture may be about 15 to 25 times, for example, about 20 times, the weight of the atorvastatin calcium to be suspended. The stirring may be performed at a temperature of about 10 to 65° C., for example, about 25 to 45° C.

Amorphous atorvastatin calcium may be obtained by dissolving crystalline atorvastatin calcium in a solvent, and adding the resulting solution to an anti-solvent. An anti-solvent is a liquid that does not dissolve atorvastatin calcium. Examples of solvents include ketones such as acetone and methyl isobutyl ketone; esters such as ethyl acetate and isopropyl acetate; chlorinated hydrocarbons such as methylene chloride and ethylene dichloride; cyclic ethers such as dioxan and tetrahydrofuran; alcohols such as methanol, ethanol and isopropanol; nitriles such as acetonitrile; dipolar aprotic solvents such as dimethylsulfoxide and dimethylformamide; and mixtures thereof with water. Examples of anti-solvents include hydrocarbons, such as cyclohexane, hexanes, heptanes, petroleum ethers, toluene, xylene and the like; dialkyl ethers such as diethyl ether, diisopropyl ether, and the like; and can readily be determined by one ordinarily skilled in the art.

An antioxidant may be added to the atorvastatin calcium solution to obtain stabilized, amorphous atorvastatin calcium.

Examples of suitable antoxidants include butylated hydroxyanisole, butylated hydroxytoluene and tertiary-butylated hydroquinone.

DETAILED DESCRIPTION OF THE INVENTION

The term 'stabilized atorvastatin calcium' means the hemicalcium salt of atorvastatin having a level of purity, which is provided and maintained through the use of antioxidants.

Stabilized, amorphous atorvastatin calcium can be obtained with purity of at least 97%, for example when determined by high performance liquid chromatography (HPLC) analysis. In general, stabilized, amorphous atorvastatin calcium having a purity of at least 99% may be obtained. In some particular embodiments, stabilized, amorphous atorvastatin calcium having a purity of at least 99.5% may be obtained.

The atorvastatin calcium solution may be dried (moisture removal) before its addition to the non-solubilizing liquid. This may be accomplished by, for example, filtration through dry molecular sieves. Alternatively or additionally, drying of the solution may be achieved by a process, wherein the solution is made using excess solvent, which is then concentrated to remove moisture from the solution.

Examples of hydroxylic solvents which may be used for dissolving atorvastatin calcium include alcohols such as methanol, ethanol, propanol, isopropanol, and mixtures thereof with water. Examples of non-hydroxylic anti-solvents which may have a higher boiling point than the hydroxylic solvent include hydrocarbons, such as cyclohexane, hexanes, heptanes, petroleum ethers, toluene, xylene and the like; dialkyl ethers such as diisopropyl ether, and the like; and can readily be determined by one ordinarily skilled in the art.

The solution of atorvastatin calcium having the desired hydroxylic solvent and non-hydroxylic anti-solvent is concentrated to remove the hydroxylic solvent either partially or completely to precipitate amorphous atorvastatin calcium. In a manner similar to that detailed above, an antioxidant may be added to the hydroxylic solution of atorvastatin calcium to obtain stabilized, amorphous atorvastatin calcium. Similarly, the atorvastatin calcium hydroxylic solution may also be treated as detailed above for moisture removal.

(4R-cis)-1,1-dimethylethyl-6-{2-[2-(4-fluorophenyl)-5-(1-methylethyl)-3-phenyl-4-[(phenylamino)-carbonyl]-1H-pyrrol-1yl]ethyl}-2,2-dimethyl-1,3-dioxane-4-acetate (Compound H, as shown in Scheme I) may be obtained by methods known in the art, such as those described in U.S. Pat. Nos. 5,003,080; 5,103,024; 5,155,251 and *Tetrahedron Lett.,* 33 (17), 2279-82 (1992), which are incorporated herein by reference.

In a particular embodiment, Compound H may be obtained as described in reaction Scheme I by
  a) treating (R)-ethyl 4-cyano-3-hydroxybutanoate (Compound A, as shown in Scheme I) with 1,1-dimethylethylacetate (Compound B, as shown in Scheme I) in the presence of n-butyl lithium and diisopropylamine to obtain (R)-1,1-dimethylethyl 6-cyano-5-hydroxy-3-oxohexanoate (Compound C, as shown in Scheme I);
  b) treating Compound C with diethyl methoxyborane and sodium borohydride to obtain [R—(R*,R*)]-1,1-dimethylethyl 6-cyano-3,5-dihydroxyhexanoate (Compound D, as shown in Scheme I);
  c) treating Compound D with 2,2-dimethoxy propane and methanesulfonic acid to obtain (4R-cis)-1,1-dimethylethyl-[6-cyanomethyl-2,2-dimethyl-1,3-dioxan]-4-acetate (Compound E, as shown in Scheme I);

d) treating Compound E under reducing conditions to obtain (4R-cis)-1,1-dimethylethyl-[6-(2-aminoethyl)-2,2-dimethyl-1,3-dioxan-4-yl]acetate (Compound F, as shown in Scheme I); and e) condensing Compound F with (±)-4-fluoro-α-(2-methyl-1-oxopropyl)-γ-oxo-N,β-diphenylbenzenebutaneamide (Compound G, as shown in Scheme I) to obtain (4R-cis)-1,1-dimethylethyl-6-{2-[2-(4-fluorophenyl)-5-(1-methylethyl)-3-phenyl-4-(phenylamino)carbonyl]-1H-pyrrol-1yl]ethyl}-2,2-dimethyl-1,3-dioxane-4-acetate (Compound H, as shown in Scheme I).

Crystalline forms of atorvastatin calcium to be used as seeds may be obtained by methods known in the art such as those described in U.S. 2002/183378, which is incorporated herein by reference, or prepared by processes exemplified herein.

In the following section embodiments are described by way of example to illustrate the process disclosed herein. However, these do not limit the scope of the present invention.

Example 1

Preparation of amorphous [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, calcium salt (2:1) (Atorvastatin Calcium Amorphous)

(4R-cis)-1,1-dimethylethyl-6-{2-[2-(4-fluorophenyl)-5-(1-methylethyl)-3-phenyl-4-[(phenylamino)-carbonyl]-1H-pyrrol-1yl]ethyl}-2,2-dimethyl-1,3-dioxane-4-acetate (Compound H)

A mixture of (4R-cis)-1,1-dimethylethyl-6-(2-aminoethyl)-2,2-dimethyl-1,3-dioxane]-4-acetate (9 Kg, 32.96 moles), (±)-4-fluoro-α-(2-methyl-1-oxopropyl)-γ-oxo-N,β-diphenylbenzenebutaneamide (13.33 Kg, 31.93 moles), n-heptane (90 L), tetrahydrofuran (22.5 L), toluene (22.5 L) and pivalic acid (2.18 Kg, 21.30 moles) was heated to reflux temperature for about 40 hrs. The reaction was monitored for completion by HPLC. The reaction mass was cooled and diluted with toluene. The reaction mixture was then washed initially with aqueous sodium hydroxide solution (0.5 N), then with aqueous hydrochloric acid solution (0.5 N) and followed by brine (10%). The organic layer was treated with activated carbon, and filtered through a hyflo filter. The organic layer was concentrated to 10% of the total volume under vacuum. Isopropyl alcohol (34 L) was then added, and the solvent recovered under vacuum, followed by repeated addition of isopropyl alcohol and solvent recovery under vacuum. The residue was dissolved in isopropyl alcohol and de-ionized water (45 L) was added till turbidity appeared. Further de-ionized water (60 L) was added gradually. The precipitated product was filtered, washed with a mixture of isopropyl alcohol and de-ionized water (2:1) and dried to get the title compound (16.2 Kg, 24.77 moles, 94% by HPLC). The crude product was purified by dissolving in isopropyl alcohol (128 L) at 50 to 55° C., concentrating the solution and cooling the residual mass slowly under stirring. The solid thus obtained was filtered, washed with chilled isopropyl alcohol and dried at 40 to 45° C. to give pure Compound H (13.2 Kg, 20.20 moles, purity: 99% by HPLC).

[R—(R*,R*)]-1,1-Dimethylethyl-2-(4-fluorophenyl)-β,δ-dihydroxy-5-(1-methylethyl)-3-phenyl-4-[(phenylamino)carbonyl]-1H-pyrrole-1-heptanoate (Compound I)

To a solution of Compound H (10 Kg, 15.29 moles) in methanol (217 L), 1 N hydrochloric acid solution (21 L, 16.04 moles) was added at 20-26° C. in 15 minutes. The reaction mixture was stirred at the same temperature until the reaction was complete (about 6 hours, monitoring by HPLC).

[R—(R*,R*)]-2-(4-Fluorophenyl)-β,δ-dihydroxy-5-(1-methylethyl)-3-phenyl-4-[(phenylamino)-carbonyl]-1H-pyrrole-1-heptanoic acid, sodium salt (Atorvastatin Sodium)

The pH of the reaction mixture obtained above was adjusted to about 12 by adding 10% w/v aqueous sodium hydroxide solution at 25-30° C. and the resulting mixture was stirred for about 6 hours at 25-30° C. The progress of the reaction was monitored by HPLC. The pH of the reaction mixture was monitored and maintained at about 12 throughout the course of the reaction by adding 10% w/v aqueous sodium hydroxide solution. After the reaction was complete, the mass was filtered and concentrated to about 84 L.

Crude [R—(R*,R*)]-2-(4-fluorophenyl)-β,δ-dihydroxy-5-(1-methylethyl)-3-phenyl-4-[(phenylamino)-carbonyl]-1H-pyrrol-1-heptanoic acid, calcium salt (2:1) (Atorvastatin Calcium Crude)

De-ionised water (89 L), methanol (19 L), and methyl tertiary butyl ether (60 L), were added to the concentrated reaction mass obtained above with continuous stirring. The layers were separated. The aqueous layer was washed with methyl tertiary butyl ether and filtered through a sparkler filter. The filtrate was collected in a reactor and its pH adjusted to 7.9-8.1 with 6 N hydrochloric acid. This mixture was heated to 48° C.

To this mixture, an aqueous solution of calcium acetate (1.33 Kg, 8.41 moles) in water (48 L) was added slowly and heated to 51° C. The contents were stirred at 51-54° C. until a clear solution was obtained. Crystalline atorvastatin calcium Form I seeds (77 g) were added and stirred. Methyl tertiary butyl ether was recovered under reduced pressure. The temperature was raised to 58° C. and de-ionised water (11 L) was added. The contents were cooled to 50° C. and a second lot of atorvastatin calcium Form I seeds (33 g) were added. The contents were further cooled slowly to 30° C. over a period of 3-4 hours and filtered. The wet cake was washed with a mixture of methanol and de-ionised water. The material was dried at 45-50° C. to yield 8 Kg of atorvastatin calcium having a purity of 97.5% determined by HPLC.

Pure Crystalline Atorvastatin Calcium

The crude product obtained above was charged to a reactor containing methanol (16 L) and tetrahydrofuran (40 L). The contents are stirred to get a clear solution and filtered through a sparkler filter followed by washing over hyflo bed with methanol (32 L). The filtrate was heated to 65° C. and refluxed for 30-60 minutes. To this, de-ionised water (about 120 L) was added slowly over a period of 1-2 hours until turbidity appeared. At the onset of turbidity, crystalline atorvastatin calcium Form I seeds (8 g) were added. The contents were stirred for 30 minutes at 68-72° C. and de-ionised water (about 40 L) was added. The contents were cooled to 50° C. and atorvastatin calcium Form I seeds (24 g) were added with continuous stirring. The contents were further cooled to 35° C. and stirred for 5 hours at 33-35° C. and then filtered. The wet cake was washed with a mixture of tetrahydrofuran, methanol and de-ionized water (volume ratio 1:1:4) and then dried at 50-55° C. under reduced pressure to yield 7.36 Kg of crystalline atorvastatin calcium.

Preparation of Crystalline Atorvastatin Calcium (Form-I)

The above dried product was added to a reactor containing de-ionized water (108.8 L) and methanol (19.2 L). The contents were stirred for 10 minutes and heated to 45° C. To this, crystalline atorvastatin calcium form I seeds (730 g) were added and the mixture was stirred at 40° C. to 45° C. until the IR spectrum of the sample was comparable with the seed crystals. The contents were filtered and washed with a mixture of de-ionized water and methanol (volume ratio 6:1). The wet cake was dried at 50-55° C. to yield 7.2 Kg of crystalline atorvastatin calcium having a purity of 99.7% determined by HPLC.

Atorvastatin Calcium Amorphous

Tetrahydrofuran (16.38 L) was added to crystalline atorvastatin calcium Form I (6.3 Kg, 5.2 moles) obtained above followed by butylated hydroxyanisole (63 g, 0.5 moles). The contents were stirred for 30 minutes at 20 to 25° C. to get a solution. This solution was filtered over a hyflo bed followed by washing of the hyflo bed with tetrahydrofuran (2.52 L), and the filtrate was collected. The filtrate was added slowly over a period of 4 to 5 hours to cyclohexane (189 L) at 25° C. The contents were stirred for 60 minutes, centrifuged and washed with cyclohexane. The material was dried under vacuum at 60° C. to 70° C. for 12 hours to yield 5.67 Kg of amorphous atorvastatin calcium having a purity of 99.54% determined by HPLC.

Example 2

Preparation of Atorvastatin Calcium Amorphous

Tetrahydrofuran (10 L) was added to atorvastatin calcium Form I (1 Kg) obtained as per Example 1 above, followed by butylated hydroxyanisole (3 g). The contents were stirred for 15 minutes at 20 to 25° C. to get a solution. This solution was filtered over hyflo bed followed by washing of the hyflo bed with tetrahydrofuran (0.4 L), and the filtrate was collected and concentrated to a volume of about 3 L at 62 to 70° C. The solution was cooled to 20° C. and added slowly over a period of 4 to 5 hours to cyclohexane (30 L) at 20 to 23° C. The contents were stirred for 60 minutes and filtered. The wet cake was washed with cyclohexane. The material was dried under vacuum at 60° C. to 70° C. for 12 hours to yield 0.9 Kg of amorphous atorvastatin calcium having a purity of 99.45% determined by HPLC.

Preparation of Crystalline Atorvastatin Calcium (Form-II)

Example 3

A mixture of methanol (180 ml) and de-ionized water (120 ml) was added to crystalline atorvastatin calcium form I (15 g) at room temperature. The temperature was raised to 25° C., seeds of crystalline atorvastatin calcium form II (1.5 g) were added, and the suspension was stirred at 25° C. The suspension became very thick after about 24 hours and a mixture of methanol (90 ml) and de-ionized water (60 ml) was added to resume stirring. The suspension was further stirred at 25° C. for another 24 hours and then filtered. The filtered solids were dried under reduced pressure at 70° C. for 48 hours to get 14.7 g of crystalline atorvastatin calcium. The XRD spectrum of the product matched with that of Form-II of atorvastatin calcium.

Example 4

A mixture of methanol (1.2 L) and de-ionized water (800 ml) was added to crystalline atorvastatin calcium Form I (100 g) at room temperature. The temperature was raised to 45° C. slowly, seeds of crystalline atorvastatin calcium form II (10 g) were added, and the suspension stirred at 45° C. The suspension became very thick after about 24 hours and a mixture of methanol (600 ml) and de-ionized water (400 ml) was added to resume stirring. The suspension was again warmed to 45° C. and further stirred at the same temperature for another 24 hours and then filtered. The filtered solids were dried under reduced pressure at 70° C. for 48 hours to get 98 g of crystalline atorvastatin calcium. The XRD spectrum of the product matched with that of Form-II of atorvastatin calcium.

Example 5

Purification of Atorvastatin Calcium (without Seeding)

The crude atorvastatin calcium obtained as per Example 1 was charged to a reactor containing methanol (16 L) and tetrahydrofuran (40 L). The contents are stirred to get a clear solution and filtered through a sparkler filter, followed by washing over hyflo bed with methanol (32 L). The filtrate was heated to 65° C. and refluxed for 30-60 minutes. To this, de-ionised water (about 120 L) was added slowly over a period of 1-2 hours until turbidity appeared. The contents were stirred for 30 minutes at 68-72° C. and de-ionised water (about 40 L) was added. The contents were cooled to 35° C. and stirred for 5 hours at 33-35° C. and then filtered. The wet cake was washed with a mixture of tetrahydrofuran, methanol and de-ionized water (volume ratio 1:1:4) and then dried at 50-55° C. under reduced pressure to yield 7.33 Kg of crystalline atorvastatin calcium.

Example 6

Preparation of Atorvastatin Calcium Amorphous

Tetrahydrofuran (480 ml) was added to crystalline atorvastatin calcium obtained above in Example 5 (60 g), followed by butylated hydroxyanisole (0.6 g). The contents were stirred, de-ionised water (24 ml) was added and the mixture was stirred for 15 minutes at 20 to 25° C. to get a clear solution. Molecular sieves (240 g, Siliporite NK30 AP® powdered) were added to the solution and the mixture was stirred for 2 hours at 20 to 25° C. This solution was filtered through a molecular sieves bed, followed by washing of the bed with tetrahydrofuran (120 ml). The filtrate was collected and concentrated to a volume of about 210 ml at 60 to 70° C. The concentrated solution was cooled to 25° C. and added slowly over a period of 2 hours to cyclohexane (1800 ml) at 22 to 25° C. under moderate stirring. The contents were stirred vigorously for 30 minutes at the same temperature and filtered. The wet cake was washed with cyclohexane (60 ml). The material was dried under reduced pressure at 60° C. to 70° C. for 6 hours to yield 54 g of amorphous atorvastatin calcium.

Siliporite NK30 AP is registered trademark of CECA, France

Example 7

Preparation of Crystalline Atorvastatin Calcium (Form II)

A mixture of methanol (1.2 L) and de-ionized water (800 ml) was added to crystalline atorvastatin calcium obtained above in example 5 (100 g) at room temperature. The temperature was raised to 45° C. slowly, seeds of crystalline atorvastatin calcium form II (10 g) were added, and the suspension stirred at 45° C. The suspension became very thick after about 24 hours and a mixture of methanol (600 ml) and de-ionized water (400 ml) was added to resume stirring. The suspension was again warmed to 45° C. and further stirred at the same temperature for another 24 hours and then filtered. The filtered solids were dried under reduced pressure at 70° C. for 48 hours to get 98 g of crystalline atorvastatin calcium. The XRD spectrum of the product matched with that of Form-II of atorvastatin calcium.

Example 8

Preparation of Atorvastatin Calcium Amorphous

Tetrahydrofuran (10 L) was added to atorvastatin calcium crystalline Form II (1 Kg) followed by butylated hydroxyanisole (3 g). The contents were stirred for 15 minutes at 20 to 25° C. to get a solution. This solution was filtered over a hyflo bed followed by washing of the hyflo bed with tetrahydrofuran (0.4 L), and the filtrate was collected and concentrated to a volume of about 3 L at 62 to 70° C. The solution was cooled to 20° C. and added slowly over a period of 4 to 5 hours to cyclohexane (30 L) at 20 to 23° C. The contents were stirred for 60 minutes and filtered. The wet cake was washed with cyclohexane. The material was dried under vacuum at 60° C. to 70° C. for 12 hours to yield 0.9 Kg of amorphous atorvastatin calcium having a purity of 99.5% determined by HPLC.

Example 9

Atorvastatin Calcium Amorphous

Methanol (100 mL) was added to atorvastatin calcium form II (10 g). The contents were stirred for 40 minutes at 20 to 25° C. to get a clear solution. Butylated hydroxyanisole (0.1 g) was then added and the mixture stirred for 30 minutes. Methanol (50 ml) was then recovered at 40° C. under reduced pressure in 30 minutes. The solution was cooled to 20 to 25° C. and added slowly over a period of one hour to cyclohexane (300 mL) at 20 to 30° C. The solution was stirred for 1 hour at 25° C. The obtained clear solution was concentrated to a volume of about 300 L at 60 to 70° C. (approximately 50 ml methanol was distilled out). The obtained suspension was then cooled to 20 to 25° C. with stirring in 30 minutes and filtered. The wet cake was washed with cyclohexane. The material was dried under vacuum at 60° C. to 70° C. for 1 hour to yield 9.0 g of amorphous atorvastatin calcium.

Example 10

Preparation of (4R-cis)-1,1-dimethylethyl-[6-(2-aminoethyl)-2,2-dimethyl-1,3-dioxan-4-yl]acetate (Compound F)

(R)-1,1-dimethylethyl-6-cyano-5-hydroxy-3-oxohexanoate (Compound C)

n-Butyl lithium and diisopropylamine are mixed at 40° C. for the formation of lithium diisopropylamine. 1,1-Dimethylethyl acetate (Compound B) in tetrahydrofuran is then added at −50° C. and the mixture stirred at −20 to 25° C. for 1 hour. The reaction mixture is further cooled to −50° C. and (R)-ethyl-4-cyano-3-hydroxybutanoate is added maintaining temperature at −20 to −25° C. and kept at the same temperature for 2 hours. The reaction is monitored for completion by thin layer chromatography. The reaction is quenched with a 2 N solution of hydrochloric acid and the product was extracted with ethyl acetate, washed with water and brine followed by complete evaporation of solvent to get the title compound which is taken to the next step without further purification.

[R—(R*,R*)]-1,1-dimethylethyl 6-cyano-3,5-dihydroxyhexanoate Compound D)

To a mixture of tetrahydrofuran and methanol containing (R)-1,1-dimethylethyl-6-cyano-5-hydroxy-3-oxohexanoate (Compound C) is added diethyl methoxyborane slowly at −80 to −90° C. and stirred for 30 minutes at the same temperature. Sodium borohydride is added in lots maintaining temperature at −80 to −90° C. and stirred for 5 hours at −80 to −90° C. After completion of reaction, the temperature is slowly raised to 0° C. then to room temperature in 2 hours, and the reaction quenched with glacial acetic acid slowly in 30 minute while maintaining temperature between 0 to 40° C. The mixture is concentrated to approximately 20% of total volume. Methanol is added and recovered to remove borane derivatives. The product is extracted with ethyl acetate, washed with water and then brine. The organic layer is concentrated to approximately 20% of original volume. Tetrahydrofuran is then added and recovered completely under reduced pressure to get the title compound as a concentrated mass, which is taken to the next step.

(4R-cis)-1,1-Dimethylethyl-[6-cyanomethyl-2,2-dimethyl-1,3-dioxan]-4-acetate (Compound E)

A mixture of 2,2-dimethoxy propane containing [R—(R*,R*)]-1,1-dimethylethyl-6-cyano-3,5-dihydroxyhexanoate (Compound D), acetone and methanesulfonic acid is stirred for 3 to 4 hours at 29 to 30° C. and the reaction monitored for completion by thin layer chromatography. The reaction is then quenched with 5% w/v aqueous sodium bicarbonate solution slowly to adjust pH to about 7 and extracted with ethyl acetate. The organic layer is concentrated and the solvent recovered completely under reduced pressure. The residue is crystallized with hexane to get the title compound as a crude product, which is recrystallized with methanol and water to get the pure compound.

(4R-cis)-1,1-Dimethylethyl-[6-(2-aminoethyl)-2,2-dimethyl-1,3-dioxan-4-yl]acetate (Compound F)

Pure (4R-cis)-1,1-dimethylethyl-[6-cyanomethyl-2,2-dimethyl-1,3-dioxan]-4-acetate (Compound E) dissolved in ammonia saturated methanol is hydrogenated in the presence of activated Raney nickel by applying hydrogen pressure of 4.5 to 5 kg/cm$^2$ at room temperature under stirring for 4 to 12 hours. The reaction is monitored for completion by gas chromatography. The catalyst is filtered through hyflo bed and concentrated to recover methanol completely under reduced pressure to get the title compound.

Example 11

Preparation of Crystalline Atorvastatin Calcium Form-I Seed

Part A—Preparation of Crude Atorvastatin Calcium

[R—(R*,R*)]-1,1-Dimethylethyl-2-(4-fluorophenyl)-β,δ-dihydroxy-5-(1-methylethyl)-3-phenyl-4-[(phenylamino)carbonyl]-1H-pyrrole-1-heptanoate (Compound I)

To a solution of Compound H (57 g) in methanol (1.71 L), 1 N hydrochloric acid solution (116 mL) was added drop wise at 20-25° C. in 15 minutes. The reaction mixture was stirred at the same temperature for about 5 hours, and monitored by TLC (hexane:ethanol::6:4). 1 N hydrochloric acid solution (10 mL) was then added and the reaction mixture was further stirred for about 2.5 hours.

[R—(R*,R*)]-2-(4-Fluorophenyl)-β,δ-dihydroxy-5-(1-methylethyl)-3-phenyl-4-[(phenylamino)-carbonyl]-1H-pyrrole-1-heptanoic acid, sodium salt (Atorvastatin Sodium)

The pH of the reaction mixture obtained above was adjusted to about 12 by adding 10% w/v aqueous sodium hydroxide solution at 25-30° C. and the resulting mixture was stirred for about 6 hours at 25-30° C. The progress of the reaction was monitored by HPLC. The pH of the reaction mixture was monitored and maintained at about 12 throughout the course of the reaction by adding 10% w/v aqueous sodium hydroxide solution. After the reaction was complete, the mass was filtered and concentrated to get the title compound as a white precipitate.

[R—(R*,R*)]-2-(4-fluorophenyl)-β,δ-dihydroxy-5-(1-methylethyl)-3-phenyl-4-[(phenylamino)-carbonyl]-1H-pyrrol-1-heptanoic acid, calcium salt (2:1) (Atorvastatin Calcium)

De-ionized water (500 mL), methanol (200 mL), and methyl tertiary butyl ether (200 mL), were added to atorvastatin sodium obtained above and stirred to obtain a solution. The layers were separated. The aqueous layer was washed with methyl tertiary butyl ether (200 mL), and filtered through hyflo bed. The hyflo bed was washed with a mixture of methanol (25 mL) and methyl tertiary butyl ether (25 mL). The filtrate was warmed to 50° C. and its pH adjusted to about 10 with concentrated hydrochloric acid. To this mixture, an aqueous solution of calcium acetate (7.52 g) in water (275 mL) was added slowly in 1.5 hours at 50° C. Some turbidity was observed at this stage. Methyl tertiary butyl ether (20 mL) was added. Some methyl tertiary butyl ether spontaneously evaporated at this stage. The mixture was heated to 80° C. to obtain a clear solution. The contents were stirred for 20 minutes at the same temperature and then allowed to cool for 1.5 hours. The contents were further cooled to 25° C. and stirred for 30 minutes at the same temperature and then filtered. The wet product was slurry washed with a mixture of methanol and de-ionized water (2:1, 100 mL) and filtered. The material was dried at 45° C. for 8 hours to yield 43.38 g of atorvastatin calcium. The XRD spectrum of the product mainly showed two very broad peaks.

Part B—Preparation of Crystalline Atorvastatin Calcium Form-I Seed

Step I

Atorvastatin calcium (2 g) obtained above was suspended in de-ionized water (20 ml) and stirred for 20 hours at about 30° C. The suspension was then filtered and dried under reduced pressure at 40 to 45° C. for 3 hours to get 1.9 g of the product. The XRD spectrum of the product showed a change in pattern from that of the starting atorvastatin calcium. An increase in sharp peaks indicating increased crystallinity was observed.

Step II

Atorvastatin calcium (1.8 g, same as that used as starting compound in step I) and atorvastatin calcium (0.2 g, obtained from step I above) were suspended in a mixture of de-ionized water (34 ml) and methanol (6 ml). The temperature was raised slowly to 38 to 40° C. and the suspension was stirred for 16 hours at the same temperature. The suspension was then cooled to 35° C., filtered and dried under reduced pressure at 40 to 45° C. for 4 hours to get 1.9 g of the product. The XRD spectrum of the product showed a change in pattern from that of the starting atorvastatin calcium. The XRD spectrum of the product matched with that of Form-I of atorvastatin calcium.

Example 12

Preparation of Crystalline Atorvastatin Calcium Form-II Seed

A mixture of methanol (360 ml) and de-ionized water (240 ml) was added to a mixture of amorphous atorvastatin calcium (15 g) and crystalline atorvastatin calcium form I (15 g), the suspension was warmed to 45° C. slowly and stirred at the same temperature. The suspension became very thick after 24 hours and a mixture of methanol (180 ml) and de-ionized water (120 ml) was added to resume stirring. The suspension was warmed to 45° C. and further stirred at the same temperature for 24 hours and then filtered. The filtered solids were dried under reduced pressure at 70° C. for 48 hours to get 27 g of crystalline atorvastatin calcium. The XRD spectrum of the product matched with that of Form-II of atorvastatin calcium.

We claim:

1. A process for the production of atorvastatin calcium in amorphous form comprising:
   a) reacting a solution of (4R-cis)-1,1-dimethylethyl-6-{2-[2-(4-fluorophenyl)-5-(1-methylethyl)-3-phenyl-4-[(phenylamino)-carbonyl]-1H-pyrrol-1yl]ethyl}-2,2-dimethyl-1,3-dioxane-4-acetate (Compound H) in a water-miscible solvent with an acid to obtain [R—(R*,R*)]-1,1-dimethylethyl-2-(4-fluorophenyl)-β,δ-dihydroxy-5-(1-methylethyl)-3-phenyl-4-[(phenylamino) carbonyl]-1H-pyrrole-1-heptanoate (Compound I);
   b) treating Compound I with an alkali metal hydroxide to obtain an alkali metal salt of atorvastatin;
   c) washing the solution of alkali metal salt of atorvastatin with a solvent immiscible or slightly miscible in water;
   d) treating the washed solution of alkali metal salt of atorvastatin with a calcium salt or calcium hydroxide to obtain atorvastatin calcium;
   e) isolating crude atorvastatin calcium;
   f) purifying crude atorvastatin calcium by dissolving in a mixture of tetrahydrofuran and methanol, and precipitating with water to obtain pure atorvastatin calcium in crystalline form; and
   g) converting crystalline pure atorvastatin calcium so obtained into amorphous form.

2. The process of claim 1, wherein the acid used is an inorganic acid.

3. The process of claim 2, wherein the acid is selected from the group consisting of hydrochloric, hydrobromic, sulphuric, phosphoric and nitric acids.

4. The process of claim 1, wherein the water-miscible solvent is selected from the group consisting of acetonitrile, alcohols, cyclic ethers, ketones and mixtures thereof.

5. The process of claim 4, wherein alcohols are selected from the group consisting of methanol, ethanol, propanol, and isopropanol.

6. The process of claim 1, wherein the reaction of step b) is carried out at a pH of about 12.

7. The process of claim 1, wherein the alkali metal hydroxide is selected from the group consisting of sodium hydroxide, potassium hydroxide and lithium hydroxide.

8. The process of claim 1, wherein the solvent immiscible or slightly miscible in water is selected from the group consisting of ethers, esters, and hydrocarbons.

9. The process of claim 8, wherein ethers are selected from the group consisting of methyl tertiary butyl ether, diethyl ether, methyl ethyl ether and dibutyl ether.

10. The process of claim 1, wherein the pH of the solution of step c) is lowered to about 7.8 to 8.2 with an acid before proceeding with step d).

11. The process of claim 1, wherein step d) is performed at a temperature of about 45 to 55° C.

12. The process of claim 1, wherein the calcium salt is selected from the group consisting of calcium acetate, calcium chloride, calcium sulfate, calcium nitrate and calcium phosphate.

13. The process of claim 1, wherein any residual solvent immiscible or slightly miscible in water remaining in the reaction mixture is removed after step d) is removed under reduced pressure.

14. The process of claim 1, wherein crude atorvastatin calcium is precipitated by addition of water.

15. The process of claim 14, wherein water is added at a temperature of about 55 to 65° C.

16. The process of claim 1, 14 or 15, wherein seeds of crystalline atorvastatin calcium are added to the reaction mixture.

17. The process of claim 1 wherein crude atorvastatin calcium is isolated by cooling the reaction mixture to a temperature of about 20 to 35° C.

18. A process for purifying atorvastatin calcium comprising dissolving crude atorvastatin calcium in a mixture of tetrahydrofuran and methanol, and precipitating with water to obtain pure atorvastatin calcium, wherein tetrahydrofuran, methanol and water are in the volume ratio 1:1:4.

19. A process for purifying atorvastatin calcium comprising dissolving crude atorvastatin calcium in a mixture of tetrahydrofuran and methanol, and precipitating with water to obtain pure atorvastatin calcium, wherein water is added at a temperature of about 60 to 65° C.

20. A process for purifying atorvastatin calcium comprising dissolving crude atorvastatin calcium in a mixture of tetrahydrofuran and methanol, and precipitating with water to obtain pure atorvastatin calcium, wherein seeds of crystalline atorvastatin calcium are added to facilitate the precipitation.

21. The process of claim 20, wherein seeds of crystalline atorvastatin calcium are added at a temperature of about 50° C.

22. The process of claim 1, wherein pure atorvastatin calcium is isolated by cooling the mixture to a temperature of about 30 to 35° C.

23. The process of claim 1, which comprises an additional step wherein the pure crystalline atorvastatin calcium obtained after step f) is suspended in a mixture of methanol and water in the volume ratio 1 to 5 and stirred with seed crystals of crystalline form I, to obtain atorvastatin calcium in crystalline form I.

24. The process of claim 23, wherein the stiffing is performed at a temperature of about 30 to 45° C.

25. The process of claim 1, which comprises an additional step wherein the pure crystalline atorvastatin calcium obtained after step f) is suspended in 15 to 25 volumes (with respect to the weight of atorvastatin calcium) of a mixture of methanol and water in the volume ratio 3 to 2 and stirred with seed crystals of crystalline form II, to obtain atorvastatin calcium in crystalline form II.

26. The process of claim 23, which comprises a further additional step wherein the obtained crystalline form I of atorvastatin calcium is suspended in 15 to 25 volumes (with respect to the weight of atorvastatin calcium) of a mixture of methanol and water in the volume ratio 3 to 2 and stirred with seed crystals of crystalline form II, to obtain atorvastatin calcium in crystalline form II.

27. The process of claim 25 or 26, wherein the stirring is performed at a temperature of about 10 to 65° C.

28. The process of claim 1, wherein amorphous atorvastatin calcium is obtained by dissolving pure crystalline atorvastatin calcium in tetrahydrofuran and adding the resulting solution to cyclohexane.

29. The process of claim 28, wherein water is added to tetrahydrofuran to dissolve pure crystalline atorvastatin calcium.

30. A process for the production of stabilized, amorphous atorvastatin calcium comprising:
   a) dissolving crystalline atorvastatin calcium and an antioxidant in a solvent;
   b) adding the atorvastatin calcium and antioxidant solution to an antisolvent; and
   c) separating precipitated, amorphous atorvastatin calcium from the resulting suspension to obtain stabilized, amorphous atorvastatin calcium.

31. A process for the production of atorvastatin calcium in amorphous form comprising:
   a) dissolving crystalline atorvastatin calcium in a hydroxylic solvent;
   b) adding the obtained solution of atorvastatin calcium to a non-hydroxylic anti-solvent, wherein the non-hydroxylic anti-solvent has a higher boiling point than the hydroxylic solvent;
   c) concentrating the solution so obtained to remove the hydroxylic solvent; and
   d) separating precipitated amorphous atorvastatin calcium from the resulting suspension to obtain amorphous atorvastatin calcium.

32. The process of claim 31, wherein an antioxidant is added to the solution of atorvastatin calcium in hydroxylic solvent.

33. The process of claim 30 or 32, wherein the antioxidant is selected from the group consisting of butylated hydroxyanisole, butylated hydroxytoluene and tertiary-butylated hydroquinone.

34. The process of claim 30 or 31, wherein the solution of atorvastatin calcium is dried before precipitation of amorphous atorvastatin calcium.

35. The process of claim 34, wherein the solution is filtered through dry molecular sieves.

36. The process of claim 34, wherein the solution is made using excess of solvent, which is then concentrated to achieve drying.

37. The process of claim 30, wherein the solvent is selected from the group consisting of ketones, esters, chlorinated hydrocarbons, cyclic ethers, alcohols, nitriles, dipolar aprtic solvents, and mixtures thereof with water.

38. The process of claim 37, wherein the cyclic ethers are selected from the group consisting of dioxan, tetrahydrofuran, and mixtures thereof.

39. The process of claim 30, wherein the anti-solvent is selected from the group consisting of hydrocarbons and dialkyl ethers.

40. The process of claim 31, wherein the hydroxylic solvent is selected from the group consisting of alcohols, and mixtures thereof with water.

41. The process of claim 37 or 40, wherein alcohols are selected from the group consisting of methanol, ethanol, propanol, and isopropanol.

42. The process of claim 31, wherein the non-hydroxylic anti-solvent is selected from the group consisting of hydrocarbons and dialkyl ethers.

43. The process of claim 39 or 42, wherein the hydrocarbons are selected from the group consisting of cyclohexane, hexane, heptane, petroleum ethers, toluene, and xylene.

44. The process of claim 1, wherein (4R-cis)-1,1-dimethylethyl-6-{2-[2-(4-fluorophenyl)-5-(1-methylethyl)-3-phenyl-4-[(phenylamino)-carbonyl]-1H-pyrrol-1yl]ethyl}-2,2-dimethyl-1,3-dioxane-4-acetate (Compound H) is obtained by
  a) treating (R)-ethyl 4-cyano-3-hydroxybutanoate (Compound A) with 1,1-dimethylethylacetate (Compound B), in the presence of n-butyl lithium and diisopropyl amine to obtain (R)-1,1-dimethylethyl-6-cyano-5-hydroxy-3-oxohexanoate (Compound C),
  b) treating Compound C with diethyl methoxyborane and sodium borohydride to obtain [R—(R*,R*)]-1,1-dimethylethyl-6-cyano-3,5-dihydroxyhexanoate (Compound D),
  c) treating Compound D with 2,2-dimethoxy propane and methanesulfonic acid to obtain (4R-cis)-1,1-dimethyl-ethyl-[6-cyanomethyl-2,2-dimethyl-1,3-dioxan]-4-acetate (Compound E),
  d) treating Compound E under reducing conditions to obtain (4R-cis)-1,1-dimethylethyl-[6-(2-aminoethyl)-2,2-dimethyl-1,3-dioxan-4-yl]acetate (Compound F), and
  e) condensing Compound F with (±)-4-fluoro-α-(2-methyl-1-oxopropyl)-γ-oxo-N,β-diphenylbenzenebutaneamide (Compound G) to obtain (4R-cis)-1,1-dimethylethyl-6-{2-[2-(4-fluorophenyl)-5-(1-methylethyl)-3-phenyl-4-(phenylamino)carbonyl]-1H-pyrrol-1yl]ethyl}-2,2-dimethyl-1,3-dioxane-4-acetate (Compound H).

45. The process of claim 1, wherein the conversion to amorphous form comprises:
  a) dissolving crystalline atorvastatin calcium and an antioxidant in a solvent;
  b) adding the atorvastatin calcium and antioxidant solution to an antisolvent; and
  c) separating precipitated, amorphous atorvastatin calcium from the resulting suspension to obtain stabilized, amorphous atorvastatin calcium.

46. The process of claim 1, wherein the conversion to amorphous form comprises:
  a) dissolving crystalline atorvastatin calcium in a hydroxylic solvent;
  b) adding the obtained solution of atorvastatin calcium to a non-hydroxylic antisolvent, wherein the non-hydroxylic anti-solvent has a higher boiling point than the hydroxylic solvent;
  c) concentrating the solution so obtained to remove the hydroxylic solvent; and
  d) separating precipitated, amorphous atorvastatin calcium from the resulting suspension to obtain amorphous atorvastatin calcium.

47. The process of claim 45 or 46, wherein an antioxidant is added to the solution of atorvastatin calcium in hydroxylic solvent.

* * * * *

UNITED STATES PATENT AND TRADEMARK OFFICE
CERTIFICATE OF CORRECTION

PATENT NO. : 7,994,343 B2
APPLICATION NO. : 10/549890
DATED : August 9, 2011
INVENTOR(S) : Yatendra Kumar, Saridi Madhava Dileep Kumar and Swargam Sathyanarayana Page 1 of 1

It is certified that error appears in the above-identified patent and that said Letters Patent is hereby corrected as shown below:

In the Specification

In Column 11, line 58, delete "at 40° C" and replace with --at -40° C--

In the Claims

In Column 15, claim 24, line 57, delete "stiffing" and replace with --stirring--

Signed and Sealed this
Thirty-first Day of December, 2013

Margaret A. Focarino
*Commissioner for Patents of the United States Patent and Trademark Office*